United States Patent [19]

Sato et al.

[11] Patent Number: 4,758,274
[45] Date of Patent: Jul. 19, 1988

[54] DENTAL AMALGAM ALLOYS CONTAINING SELENIUM

[75] Inventors: Atsushige Sato, No. 4-24-3-701, Asagayakita, Suginami-ku, Tokyo; Ishi Miura, No. 3-21-6, Kamimeguro, Meguro-ku, Tokyo; Yasuhiro Kumei, Tokyo; Osamu Okuno, Narashino; Tsuyoshi Nakano, Chiba; Yoshinobu Yamamura, Kawasaki, all of Japan

[73] Assignees: Atsushige Sato; Ishi Miura; G-C Dental Industrial Corp., all of Tokyo, Japan

[21] Appl. No.: 26,193

[22] Filed: Mar. 16, 1987

[30] Foreign Application Priority Data

Mar. 31, 1986 [JP] Japan .................................. 61-71119

[51] Int. Cl.$^4$ .............................................. C22C 5/08
[52] U.S. Cl. ..................................................... 75/255
[58] Field of Search .................................. 75/251–255; 420/504, 503

[56] References Cited

U.S. PATENT DOCUMENTS 4,528,034  7/1985  Sato et al. ............................. 75/255

FOREIGN PATENT DOCUMENTS 155337   7/1982  Japan .
171540  10/1983  Japan .
2099455 12/1982  United Kingdom .
2121823  1/1984  United Kingdom .

*Primary Examiner*—Christopher W. Brody
*Attorney, Agent, or Firm*—Oblon, Fisher, Spivak, McClelland & Maier

[57] ABSTRACT

A dental amalgam alloy containing selenium includes one or two or more of powders of chemically synthesized copper selenides (CuSe, $Cu_2Se$), silver selenide ($Ag_2Se$), gold selenide ($Au_2Se_3$), nickel selenide (NiSe), palladium selenides (PdSe, $PdSe_2$), platinum selenides ($PtSe_2$, $PtSe_3$), zinc selenide (ZnSe), mercury selenide (HgSe), indium selenide ($In_2Se_3$) and tin selenide (SnSe) added to and mixed with a dental amalgam alloy powder with the resulting powder mixture containing selenium regulated to an amount of 0.05 to 5 weight %.

1 Claim, 2 Drawing Sheets

DENTAL AMALGAM ALLOYS CONTAINING SELENIUM

BACKGROUND OF THE INVENTION

1. Field of the Invention

The present invention relates to a dental amalgam alloy containing selenium.

2. Statement of the Prior Art

In using the dental amalgam, the alloy powder composed mainly of silver, tin and copper is amalgamated with mercury, and the resulting amalgam is filled in an oral cavity for setting or curing therein.

The high-copper type amalgam alloys including the dispersion-enhanced type amalgam alloys are used as the amalgam alloys in which no crystallization of the $Sn_{7-8}Hg(\gamma_2)$ phase takes place. These alloys have their copper content increased whereby the crystallization of a $Cu_3Sn(\epsilon)$ or $Cu_6Sn_5(\eta)$ phase is effected without crystallizing the $Sn_{7-8}Hg(\gamma_2)$ phases, resulting in improvements in their mechanical properties. Such improvements give weight to the mechanical properties and corrosion resistance of the cured amalgam. However, any close attention is not paid at all to cytotoxicity resulting from mercury eluting from the amalgam filler.

In recent years, amalgam alloys containing selenium have been proposed in Japanese Patent Laid-Open Publication Nos. 57(1982)-155337 and 58(1983)-171540 in view of the fact that selenium has been found to be an element effective for eliminating cytotoxicity ascribed to mercury in amalgam fillers, and the fact that the triturated amalgams are effective for the elimination of cytotoxicity has been read in and ascertained the academic society.

According to one method for making the dental amalgam alloys containing selenium that has been made public, selenium is dissolved and incorporated into the respective constitutional metals of amalgam alloys, silver alloys or copper alloys, when they are dissolved for alloying. According to another method, the constitutional components are coated on the surface of selenium. According to still another method, selenium powders are directly added to and mixed with the amalgam alloys prepared in the ordinary process. It is considered, however, that these methods are not the best, taking into account the toxicity of selenium vapors or oxides expected to be formed due to a low melting point (689° C.) when selenium is dissolved into molten alloys, the ununiform distribution of selenium caused due to its low specific gravity (about 4.2) during mixing.

SUMMARY OF THE INVENTION

The present invention has for its object to provide a safe and simple method for making dental amalgam alloys containing selenium in which the amount of selenium to be contained is accurately adjusted, and in which selenium is uniformly distributed.

When it is intended to use amalgam in dentistry, reductions in the amount of mercury eluting from the amalgam into saliva in the oral cavity are desired in terms of both living body of a patient and prevention of mercury pollution in ecology (the environmental problem), even though the cytotoxicity of mercury is eliminated by the antagonism of selenium contained in the selenium-containing amalgam used. To that end, the selenium-containing amalgam alloys are improved so as to reduce or limit the amount of mercury eluting from the selenium-containing amalgams.

In accordance with the present invention, the powders of a selenium-containing substance or material is added to and mixed with the powders of an amalgam alloy prepared in the ordinary process in order to pour selenium into the amalgam alloy. If a selenium-containing substance having its specific gravity close to that (about 9) of the amalgam alloy is selected in this case, it is then possible to make the amalgam alloy containing selenium, in which selenium is evenly distributed in the amalgam alloy particles, by regulating both components to the same particle size.

BRIEF DESCRIPTION OF THE DRAWINGS

The above and other objects and features of the present invention will become apparent from the following detailed description with reference to the accompanying drawings which are given for the purpose of illustration alone and in which:

FIG. 1 illustrative of those cells before treatment,

FIG. 2 illustrative of those cells applied with the amalgam of Comparison Example 2 and FIG. 3 illustrative of those cells applied with the amalgam of Example 12.

DETAILED DESCRIPTION OF THE INVENTION

Figure 1:
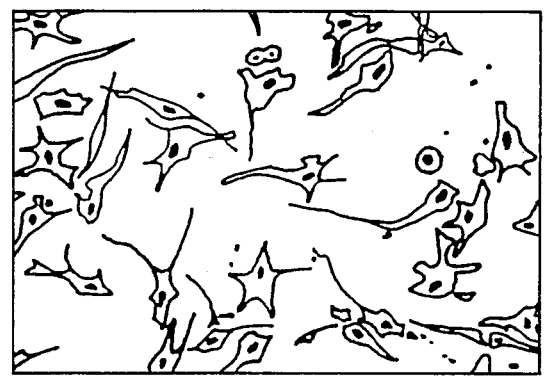
FIGS. 1 to 3 are phase-contrast microphotographs of the L-strain cell cultured.

As the selenium-containing substances use is made of stable selenides prepared stoichiometrically according to the known chemical synthesis processes. Since such preparation may be carried out substantially in a closed state, it is possible to prevent environmental pollution due to selenium dilution as much as possible. In addition, such selenides make the addition of an accurate amount of selenium possible, because they have a stoichiometrically uniform composition.

Owing to the fact that the selenide or selenides are stoichiometrically firmly bonded, it is also expected that if a metal bonded to selenium is selected, selenium is then efficiently bonded to mercury in the amalgam and to have an effect upon the prevention of eluting mercury from the amalgam.

In the present invention, the dental amalgam alloys containing selenium are prepared by adding at least one of selenides of copper, silver, gold, nickel, palladium, platinum, zinc, mercury, indium or tin ($CuSe$, $Cu_2Se$, $Ag_2Se$, $Au_2Se_3$, $NiSe$, $PdSe$, $PdSe_2$, $PtSe_2$, $PtSe_3$, $ZnSe$, $HgSe$, $In_2Se_3$, $SnSe$) to the amalgam alloy powders prepared in the ordinary processes. These metal elements form stable selenides, which are in turn to be selected on the basis that they show a specific gravity close to that (about 9) of the amalgam alloys, and that they provide amalgams reducing the amount of elution of mercury, compared with those in which selenium is incorporated in the conventional manner. By way of example, $Ag_2Se$ has a specific gravity of 8.0 close to that of the amalgam alloy, and forms a stable compound. The particle size of such selenides is regulated to that of the amalgam alloy powder for sufficient mixing, whereby it is possible to prepare a selenium-containing amalgam alloy powder in which selenium is distributed uniformly.

Since the dental amalgam alloy containing selenium prepared in this manner includes the selenide or selenides chemically firmly bonded thereto in advance, it is presumed that when that alloy is amalgamated with mercury, selenium takes on the form of a metallic compound, which limits the non-metallic property of selenium and is to be easily assimilated by mercury in the amalgam. Accordingly, since selenium and mercury are uniformly distributed in the triturated amalgam, it is expected that the antagonism of selenium for eliminating the cytotoxicity of mercury is effectively exerted, and that selenium is bonded to mercury through the metal forming the selenide(s) to have an effect upon reductions in the amount of elution of mercury. It goes without saying that the amalgam maintains an increase in its initial strength brought about by the incorporation of selenium.

In the following, the present invention will be explained with the examples given for the purpose of illustration alone.

EXAMPLES

In the performance testing of the dental amalgam alloys containing selenium, two types of amalgam alloy powders, one having a composition of 70% of silver, 27% of tin and 3% of copper and the other a composition of 56% of silver, 29% of tin and 15% of copper, were provided for the purpose of comparing the test samples with the selenide powders (Examples 1 to 12) to those without any selenide powder (Comparison Examples 1 and 2). In the testing of the elution of mercury from the selenium-containing amalgam, for instance, the amalgam alloy powders added and mixed with pure selenium powders (Comparison Example 3) were compared with those added and mixed with various selenide powders (Examples 4–5 and 10).

First, the fine alloy powders used in Comparison Exmples 1 and 2 were obtained by melting the alloys having the aforesaid compositions, atomizing them in a nitrogen stream and passing them through a 270-mesh sieve.

COMPARISON EXAMPLE 1

A sample was prepared by adding mercury to an amalgam alloy powder composed of 70% of silver, 27% of tin and 3% of copper in a weight ratio of 0.75 to 1, followed by mechanical trituration for 10 sec. with an amalgamator.

COMPARISON EXAMPLE 2

A sample was prepared by adding mercury to an amalgam alloy powder composed of 56% of silver, 29% of tin and 15% of copper in a weight ratio of 0.83 to 1, followed by mechanical trituration for 15 sec. with an amalgamator.

COMPARISON EXAMPLE 3

Zero point one (0.100) g of a selenium powder passing through a 270-mesh sieve was added to and mixed with 50 g of the amalgam alloy used in Comparison Example 2 to prepare an amalgam alloy containing 0.2% of selenium. A sample was prepared by adding mercury to this selenium-containing amalgam alloy in a weight ratio of 0.83 to 1, followed by mechanical trituration for 15 sec. with an amalgamator.

EXAMPLE 1

Zero point three-seven-three (0.373) g of a silver selenide powder passing through a 270-mesh sieve were added to and mixed with 50 g of the amalgam alloy used in Comparison Example 1 to prepare an amalgam alloy containing 0.2% of selenium. A sample was prepared by adding mercury to this selenium-containing amalgam alloy in a weight ratio of 0.75 to 1, followed by mechanical trituration for 10 sec. with an amalgamator.

EXAMPLE 2

Zero point nine-three-three (0.933) g of a silver selenide powder passing through a 270-mesh sieve were added to and mixed with 50 g of the amalgam alloy used in Comparison Example 1 to prepare an amalgam alloy containing 0.5% of selenium. A sample was prepared by adding mercury to this selenium-containing amalgam alloy in a weight ratio of 0.75 to 1, followed by mechanical trituration for 10 sec. with an amalgamator.

EXAMPLE 3

One point eight-seven (1.87) g of a silver selenide powder passing through 270-mesh sieve were added to and mixed with 50 g of the amalgam alloy used in Comparision Example 1 to prepare an amalgam alloy containing 1.0% of selenium. A sample was prepared by adding mercury to this selenium-containing amalgam alloy in a weight ratio of 0.75 to 1, followed by mechanical trituration for 10 sec. with an amalgamator.

EXAMPLE 4

Zero point three-seven-three (0.373) g of a silver selenide powder passing through a 270-mesh sieve were added to and mixed with 50 g of the amalgam alloy used in Comparison Example 2 to prepare an amalgam alloy containing 0.2% of selenium. A sample was prepared by adding mercury to this selenium-containing amalgam alloy in a weight ratio of 0.83 to 1, followed by mechanical trituration for 15 sec. with an amalgamator.

EXAMPLE 5

Zero point one-eight (0.180) g of a copper selenide (CuSe) powder passing through a 270-mesh sieve were added to and mixed with 50 g of the amalgam alloy used in Comparison Example 2 to prepare an amalgam alloy containing 0.2% of selenium. A sample was prepared by adding mercury to this selenium-containing amalgam alloy in a weight ratio of 0.83 to 1, followed by mechanical trituration for 15 sec. with an amalgamator.

EXAMPLE 6

Zero point one-seven-four (0.174) g of a nickel selenide powder passing through a 270-mesh sieve were added to and mixed with 50 g of the amalgam alloy used in Comparison Example 2 to prepare an amalgam alloy containing 0.2% of selenium. A sample was prepared by adding mercury to this selenium-containing amalgam alloy in a weight ratio of 0.83 to 1, followed by mechanical trituration for 15 sec. with an amalgamator.

EXAMPLE 7

Zero point one-eight-two (0.182) g of a platinum selenide ($PtSe_3$) powder passing through a 270-mesh sieve were added to and mixed with 50 g of the amalgam alloy used in Comparison Example 2 to prepare an amalgam alloy containing 0.2% of selenium. A sample was prepared by adding mercury to this selenium-con taining amalgam alloy in a weight ratio of 0.83 to 1, followed by mechanical trituration for 15 sec. with an amalgamator.

EXAMPLE 8

Zero point one-three (0.130) g of a copper selenide ($Cu_2Se$) powder and 0.117 g of a palladium selenide (PdSe) powder, each passing through a 270-mesh sieve, were added to and mixed with 50 g of the amalgam alloy used in Comparison Example 2 to prepare an amalgam alloy containing 0.2% of selenium. A sample was prepared by adding mercury to this selenium-containing amalgam alloy in a weight ratio of 0.83 to 1, followed by mechanical trituration for 15 sec. with an amalgamator.

EXAMPLE 9

Zero point zero-nine (0.090) g of a copper selenide (CuSe) powder and 0.133 g of a gold selenide powder, each passing through a 270-mesh sieve, were added to and mixed with 50 g of the amalgam alloy used in Comparison Example 2 to prepare an amalgam alloy containing 0.2% of selenium. A sample was prepared by adding mercury to this selenium-containing amalgam alloy in a weight ratio of 0.83 to 1, followed by mechanical trituration for 15 sec. with an amalgamator.

EXAMPLE 10

Zero point zero-nie (0.090) g of a zinc selenide powder, 0.044 g of a palladium selenide ($PdSe_2$) powder and 0.055 g of platinum selenide ($PtSe_2$), each passing through a 270-mesh sieve, were added to and mixed with 50 g of the amalgam alloy used in Comparison Example 2 to prepare an amalgam alloy containing 0.2% of selenium. A sample was prepared by adding mercury to this selenium-containing amalgam alloy in a weight ratio of 0.83 to 1, followed by mechanical trituration for 15 sec. with an amalgamator.

EXAMPLE 11

Zero point one-three (0.130) g of a copper selenide ($Cu_2Se$) powder, 0.050 g of an indium selenide powder and 0.045 g of a platinum selenide ($PtSe_3$) powder, each passing through a 270-mesh sieve, were added to and mixed with 50 g of the amalgam alloy used in Comparison Example 2 to prepare an amalgam alloy containing 0.2% of selenium. A sample was prepared by adding mercury to this selenium-containing amalgam alloy in a weight ratio of 0.83 to 1, followed by mechanical trituration for 15 sec. with an amalgamator.

EXAMPLE 12

Zero point zero-nine-three (0.093) g of a silver selenide powder, 0.063 g of a tin selenide powder, 0.090 g of a mercury selenide powder and 0.055 g of a platinum selenide ($PtSe_2$) powder, each passing through a 270-mesh sieve, were added to and mixed with 50 g of the amalgam alloy used in Comparison Example 2 to prepare an amalgam alloy containing 0.2% of selenium. A sample was prepared by adding mercury to this selenium-containing amalgam alloy in a weight ratio of 0.83 to 1, followed by mechanical trituration for 15 sec. with an amalgamator.

The testing results of these amalgam alloys containing selenium are set forth in the following Table in which the examples according to the present invention are compared with the comparison examples.

TABLE

| | Working Time (min.) | Compressive Strength ($kgf/cm^2$) | | Flow (%) | Cytotoxicity |
| --- | --- | --- | --- | --- | --- |
| | | After 30 min. | After 24 hours | | |
| Comparison Example 1 | 8 | 400 | 4640 | 1.42 | Severe |
| Comparison Example 2 | 6 | 1260 | 5950 | 0.31 | " |
| Comparison Example 3 | 6 | 1590 | 5920 | 0.16 | No |
| Example 1 | 8 | 630 | 4730 | 0.70 | " |
| Example 2 | 8 | 660 | 4730 | 0.68 | " |
| Example 3 | 8 | 680 | 4600 | 0.68 | Slight |
| Example 4 | 6 | 1490 | 5910 | 0.20 | No |
| Example 5 | 6 | 1570 | 5890 | 0.19 | " |
| Example 6 | 6 | 1510 | 5870 | 0.20 | " |
| Example 7 | 6 | 1590 | 5920 | 0.16 | " |
| Example 8 | 6 | 1590 | 5890 | 0.19 | " |
| Example 9 | 6 | 1520 | 5960 | 0.21 | " |
| Example 10 | 6 | 1630 | 5920 | 0.16 | " |
| Example 11 | 6 | 1600 | 5900 | 0.16 | " |
| Example 12 | 6 | 1580 | 5940 | 0.19 | " |

In the table, the "working time" refers to a time for which each sample is condensed and easily carved in the teeth mode, while the compressive strength and flow were measured according to ADA standard No. 1. The cytotoxicity testing was performed in accordance with the in vitro cell culture method using L-strain cells. The amount of mercury dissolved from the amalgam was analyzed in accordance with the method of JIS-K-0102. The influence of addition of the selenides to the amalgam alloys was determined by the comparison of Comparison Example 1 with Examples 1–3 and Comparison Example 2 with Examples 4–12 in terms of both physical properties such as compressive strength and flow, and cytotoxicity. The relation between the selenium-containing amalgam alloys prepared by the present invention and those disclosed in Japanese Patent Laid-Open Publication No. 57(1982)-155337 was examined by the comparison of Comparison Example 3 with Examples 1–12 in terms of both the physical properties and cytotoxicity.

Referring now to the effect exerted upon the physical properties by the incorporation of selenium, it is evidently found from the comparison of the compressive strength after 30 minutes set forth in Table 1 that such strength is larger in Examples 1 to 3 than in Comparison Example 1, and in Examples 4 to 12 than in Comparison Example 2, and that the degree of flow decreases in association with this, which means that improvements are introduced into the physical properties. This fact indicates that after the amalgams of the present invention have been filled in the oral cavity, they have their physical properties effective for the break down caused by the initial occlusal pressure. Similar improvements in the physical properties are found in the triturated selenium-containing amalgam of Comparison Example 3. From this, it is ascertained that the dental amalgam alloys containing selenium prepared according to the present invention provide triturated amalgams having their physical properties similar to those of the alloy disclosed in Japanese Patent Laid-Open Publication No. 57-155337.

Turning on the other hand to the effect upon the cytotoxicity by the incorporation of selenium, it is found that while Comparison Examples 1 and 2 free from selenium show severe toxicity, Example 1 to 12, in which selenide is added, show almost no toxicity, as is the case with Comparison Example 3 in which selenium is added, this means that the toxicity decreases to a sufficient level.

Figure 2:
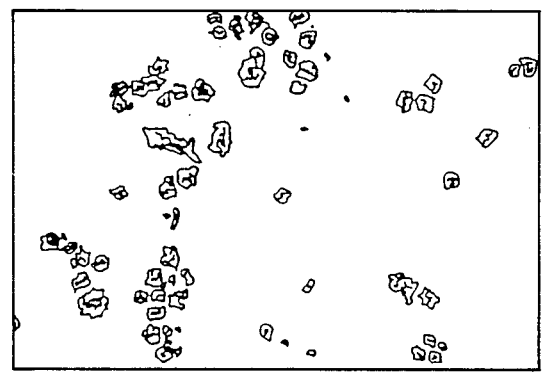
Figure 3:
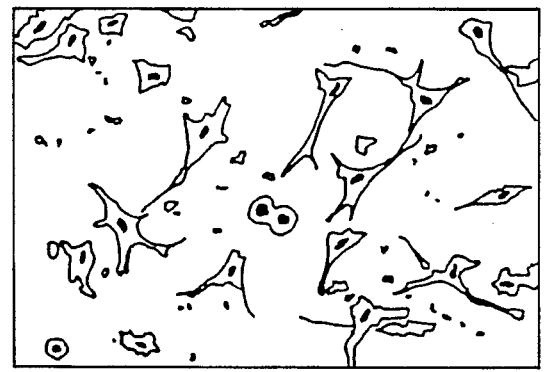

In what follows, the typical examples of cytotoxicity will be explained with reference to FIGS. 1 to 3. FIG. 1 is a phase-contrast microphotograph showing normally cultured L-strain cells. FIG. 2 is a similar view showing L-strain cells to which the triturated amalgam of Comparison Example 2 is added, which indicates that all the cells are damaged because of its severe toxicity. On the other hand, FIG. 3 is a similar view showing normally cultured L-strain cells to which the triturated amalgam of Example 12 is added, from which it is clearly found that the cells are microphotographically equivalent to the normal cells owing to the disappearance of cytotoxicity.

The triturated amalgams obtained from the dental amalgam alloys containing selenium prepared according to the present invention bring about an increase in the initial strength, as compared with those free from selenium, and allow the antagonism of selenium for eliminating the cytotoxicity of mercury to be satisfactorily produced.

The tests of elution of mercury from the triturated amalgams containing selenium were performed in the following manner. First, the elution test sample was made by filling each triturated amalgam in an acryl plate ($10 \times 50 \times 3$ mm) having five holes of 5 mm in diameter and smoothening the upper and lower face thereof after 2 minutes. Ten minutes later, the acryl plate was immersed in artificial saliva. Each sample was immersed for 1, 3, 7, 15, 30 and 60 days, and was stored in a constant-temperature chamber of 37° C. Thereafter, the amount of elution of mercury per surface area of each amalgam was measured. The artificial saliva used was of the composition proposed by Greenwood and specified below.

| | |
|---|---|
| KCl | 2.4 g |
| $Ca_3(PO_4)_2$ | 0.6 g |
| $K_2SO_4$ | 0.9 g |
| $Na_3PO_4.12H_2O$ | 0.8 g |
| Albumin | 5.0 g |
| Water | 1000 ml |

Figure 4:
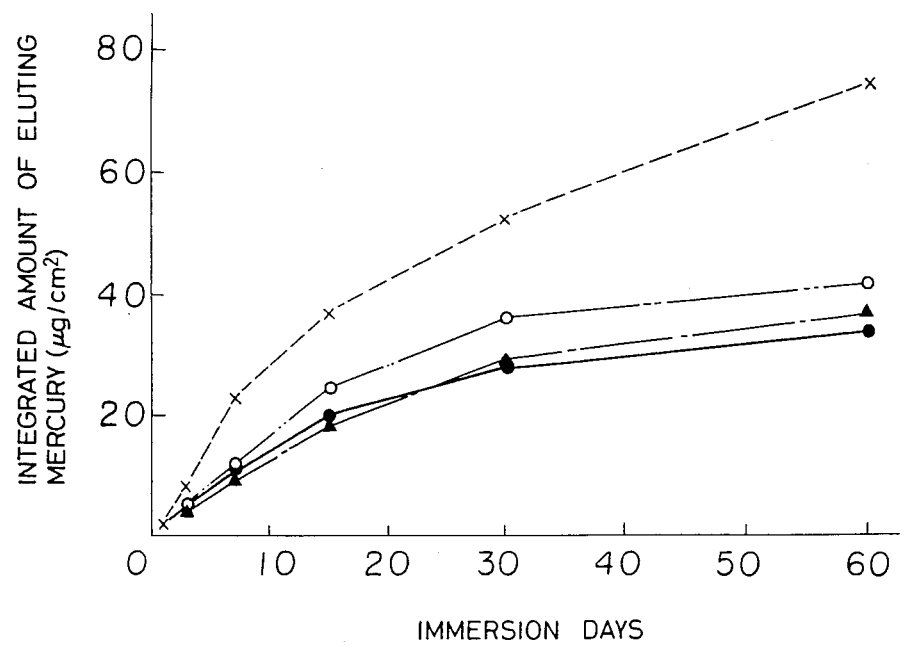
FIG. 4 shows the integrated values of the amount of mercury from the amalgams of Examples 4, 5 and 10 as well as Comparison Example 3 into artificial saliva.

A part of the results is set forth in FIG. 4 which shows the relation between immersion days and integrated amount of eluting mercury, and in which ●, ▲, ○ and × stand for Examples 4, 5 and 10 and Comparison Example 3, respectively. From FIG. 4, its is found that the selenium-containing amalgams (Examples 4, 5, 10) to which various selenides are added, start to decrease in the amount of eluting mercury from after approximately one week, and decrease in that amount to about one-half of that of the selenium-containing amalgam of Comparison Example 3 to which pure selenium is added.

The dental amalgam alloys containing selenium prepared according to the present invention provide alloy powders having a uniform selenium distribution, and are effective in view of the protection of workers against poisonous selenium vapors or oxides expected to be produced at the time of their production. In addition, the products obtained by trituration the selenium-containing amalgam alloys with mercury are smaller in the amount of eluting mercury than those prepared in the known processes, and are expected to make a contribution to the prevention of mercury pollution in ecology and environment. Hence, the dental amalgam alloys containing selenium according to the present invention are safely produced, do not give the cytotoxicity of mercury to patients during treatment due to the antagonism of selenium, and are safe in view of the prevention of environmetal mercury pollution after treatment, since the amount of mercury eluting from the triturated amalgams is reduced or limited. Thus, the dental amalgamating alloys according to the present invention are safe in every respect, and makes a great deal of contribution of the dental field.

What is claimed is:

1. An alloy mixture for dental amalgam comprising mainly silver and tin and including one or more of copper, zinc, indium, palladium, platinum, gold, cobalt, nickel, germanium and mercury, and selenium wherein at least one powder of chemically synthesized copper selenides (CuSe, $Cu_2Se$), silver selenide ($Ag_2Se$), gold selenide ($Au_2Se_3$), nickel selenide (NiSe), palladium selenides (PdSe, $PdSe_2$), platinum selenides ($PtSe_2$, $PtSe_3$), zinc selenide (ZnSe), mercury selenide (HgSe), indium selenide ($In_2Se_3$) and tin selenide (SnSe) is added to and mixed with an alloy for dental amalgam powder comprising mainly silver and tin and including one or more of copper, zinc, indium, palladium, platinum, gold, cobalt, nickel, germanium and mercury, the resulting powder mixture containing selenium in an amount of 0.05 to 5 weight %.

* * * * *